United States Patent [19]

Cooper et al.

[11] Patent Number: 5,196,345
[45] Date of Patent: Mar. 23, 1993

[54] METHOD FOR CONTROLLING THE REMOVAL OF ACIDIC METAL CARBONYL HYDRIDE FROM PRODUCT STREAMS

[75] Inventors: James L. Cooper; Jack M. Bogle, both of Longview, Tex.

[73] Assignee: Eastman Kodak Company, Rochester, N.Y.

[21] Appl. No.: 662,132

[22] Filed: Feb. 28, 1991

Related U.S. Application Data

[62] Division of Ser. No. 231,566, Aug. 12, 1988, Pat. No. 5,091,317.

[51] Int. Cl.$^5$ ............................................. G01N 33/20
[52] U.S. Cl. ............................................ 436/55; 436/73; 436/150; 436/163; 422/76; 422/82.02; 422/105
[58] Field of Search ............... 436/73, 55, 43, 150, 436/163; 422/76, 82.02, 82.03, 105, 108; 435/289; 204/45.5

[56] References Cited

U.S. PATENT DOCUMENTS

| | | | |
|---|---|---|---|
| 3,926,738 | 12/1975 | Nyiri et al. | 435/289 |
| 4,011,297 | 3/1977 | Nyman et al. | 423/24 |
| 4,053,743 | 10/1977 | Niemi | 364/500 |
| 4,167,450 | 9/1979 | Chesbro et al. | 435/3 |
| 4,390,729 | 6/1983 | Oswald | 568/454 |
| 4,686,189 | 8/1987 | Redikultsev et al. | 435/289 |
| 4,935,348 | 6/1990 | oosterhuis et al. | 435/3 |
| 4,952,406 | 8/1990 | Brown et al. | 514/425 |

Primary Examiner—James C. Housel
Assistant Examiner—Lyle A. Alexander
Attorney, Agent, or Firm—Mark A. Montgomery; William P. Heath, Jr.; S. E. Reiter

[57] ABSTRACT

A method for determining the concentration of an acidic metal carbonyl hydride in an organic liquid by measuring the conductivity or pH of the liquid. The air addition to a continuous air demetallating unit may be controlled by feedback from the conductivity or pH measurement of the effluent.

8 Claims, No Drawings

METHOD FOR CONTROLLING THE REMOVAL OF ACIDIC METAL CARBONYL HYDRIDE FROM PRODUCT STREAMS

This is a divisional of copending application Ser. No. 07/231,566 filed on Aug. 12, 1988 now U.S. Pat. No. 5,091,317.

BACKGROUND OF THE INVENTION

1. Field of the Invention

The present invention relates to a method for measuring the amount of acidic metal carbonyl hydrides and derivatives thereof in a liquid. In one aspect, it pertains to the relationship between the transition metal carbonyl hydride concentration in an organic stream and the conductivity and/or the pH of the stream. In another aspect, it pertains to a method of controlling the air demetallating of a crude product stream by measurement of either the conductivity or pH of the demetallated stream.

2. Description of the Background

Catalytic processes involving acidic transition metal carbonyl hydrides and derivatives thereof are well known. For example, acidic metal carbonyl hydrides are active catalysts for the homologation of alcohols, the carbonylation of cyclic ethers, dialkyl acetals, ortho esters, and esters, and the hydrogenation, hydrosilation, hydrocarboxylation, and hydroformylation of alkenes. Typical metal carbonyl hydrides employed for such reactions include those of the metals of Groups VI, VII, and VIII. For example, the hydroformylation or oxo process is used for the preparation of oxygenated organic compounds by the reaction of carbon monoxide and hydrogen (synthesis gas) with carbon compounds containing olefinic linkages in the presence of a carbonylation catalyst. Reaction conditions typically comprise synthesis gas pressures of from about 1500 to 4500 psig and temperatures of from about 150° to 450° F.

The oxo process is a particularly attractive method for the preparation of valuable aldehydes. A great variety of olefins may be used in the process. Thus, straight- and branched-chain olefins and diolefins, olefinic fractions from the hydrocarbon synthesis process, thermal or catalytic cracking operations, and other sources of hydrocarbon fractions containing olefins may be used as starting materials. Not only olefins, but most organic compounds possessing at least one non-aromatic carbon-carbon double bond may also be reacted by this method. Typically, the catalyst may be added in the form of a cobalt compound such as cobalt carbonyl, a cobalt soap, or a phosphine coordination complex of a cobalt compound. Under the conditions of the reaction, the catalyst is present as an acidic cobalt carbonyl hydride, e.g., $HCo(CO)_4$ or $HCo(CO)_3PR_3$. Catalysts which do not contain alkyl or aryl phosphine ligands are generally referred to as unmodified catalysts. The oxo process is discussed in great detail in U.S. Pat. Nos. 3,518,319 and 3,239,569, which are incorporated by reference herein.

Efficient recycling of the catalysts often requires that the catalyst be removed from the crude product before purification of the product. For example, distillation of a crude product before removal of an acidic metal carbonyl hydride may result in loss of catalyst due to thermal decomposition.

In particular, the unmodified cobalt carbonyl catalyst has been widely used for synthesis of aldehydes by the oxo process using what is generally referred to as an overflow reactor design. The crude aldehyde, reaction solvent, and cobalt carbonyl hydride as effluent from the oxo reactor are sent to the crude aldehyde refining distillation columns. It is well known in the art that the cobalt carbonyl hydride contained in the crude aldehyde product stream must be removed prior to aldehyde rectification. Thermal treatment of the cobalt carbonyl hydride in the base of the aldehyde rectification column results in the decomposition of the cobalt carbonyl hydride to metal plate, and to some degree a small quantity of cobalt carbonyl hydride will volatilize into the overhead product. In either case the addition of cobalt carbonyl hydride to the base of an aldehyde rectification column is undesirable.

A number of methods have been devised for the recovery and recycling of cobalt catalysts from organic streams. U.S. Pat. No. 3,369,050 discloses the process of distilling the product from the catalyst in the presence of a controlled concentration of a protecting agent such as a mixture of propylene and carbon monoxide, and thereby protecting the catalyst from decomposition. U.S. Pat. No. 3,539,634 describes the removal of tarry constituents from the liquid residue after distillation by passing the residue over a solid adsorbent which is effective in selective adsorption of the tarry constituents without significant adsorption of the catalyst. The use of a cobalt catalyst which is supported on alumina and is thus easily separable from the product stream is disclosed in U.S. Pat. No. 3,991,119. U.S. Pat. No. 4,060,557 describes the use of a wiped film evaporator for separating the products from the catalysts. The evaporator has rotating wiper blades which mechanically produce a thin film and continuously wipe this film on a heated surface. This mechanical wiping action provides a more rapid removal of the catalyst residue or bottoms. The process thus allows for minimal build-up of catalyst residue, reduced catalyst decomposition, and rapid continuous processing.

A preferred process for catalyst recovery from the product stream involves treating the product stream with oxygen to convert the cobalt carbonyl hydride to a water soluble cobalt salt. The cobalt salt may then be removed from the product stream by contact with water. This process is known as air decobalting. U.S. Pat. No. 4,225,458 teaches a method for the regeneration of the catalyst from the cobalt salt which comprises contacting the water solution of the cobalt salt with a soap derived from the heavy oxygenated bottoms fraction from the distillation unit.

Of the above-mentioned methods for the recovery of recycle of the cobalt catalyst, the air decobalting method is preferred. However, the quantity of air used for the decobalting must be controlled. As disclosed in U.S. Pat. No. 3,409,648, addition of excess air to the product stream results in oxidation of desired aldehyde product to undesired carboxylic acid. Thus, the quantity of air added to the product stream must be limited to the minimum amount necessary to convert all of the cobalt carbonyl hydride to cobalt salts. Addition of too little air will result in incomplete conversion of cobalt carbonyl hydride to cobalt salts and loss of valuable catalyst through decomposition in the distillation step. Addition of too much air will result in oxidation of the desired aldehyde product to undesired carboxylic acid.

Minimizing the quantity of air added in the decobalting step requires a method for measuring the degree of conversion of the cobalt carbonyl hydride to cobalt salts in the product stream. For use in a continuous air decobalting unit, a fast method of measuring the conversion of cobalt carbonyl hydride to cobalt salts which can be used in a feedback system is especially desirable. With such a method of measurement the quantity of air added in the decobalting step could be minimized even when the concentration of cobalt carbonyl hydride in the product stream or the liquid flow rate of the product stream are unknown or change with time.

To date, the analytical methods used to determine the degree of conversion of cobalt carbonyl hydride to cobalt salts have included wet-chemistry techniques and/or well known instrumental techniques including atomic adsorption and emission spectroscopy, ultraviolet spectroscopy, and infrared spectroscopy. Each of these methods suffers from drawbacks which make their utilization undesirable. For example, the wet chemistry analytical methods are cumbersome, time-consuming, and ill suited for use as a means of feedback in a continuous air decobalting unit. Measurements based on atomic absorption and emission spectroscopy determine only the total cobalt concentration, and, thus, do not provide any information on the degree of conversion of cobalt carbonyl hydride to cobalt salts. Measurements using ultra-violet or infrared spectroscopy require either cumbersome sample preparation which would be ill suited for a continuous system or expensive high-pressure windows, since the stream is under pressure.

Thus, there is a need for a method of determining the amount of acidic metal carbonyl hydride in the product stream of a catalytic process which can be used as a means of feedback in a continuous catalyst removing unit. In particular, there is a need for a method of measuring the degree of conversion of cobalt carbonyl hydride to cobalt salts in the product stream of the oxo process which can be used as a means of feedback in a continuous air decobalting unit.

SUMMARY OF THE INVENTION

In accordance with the present invention, it has been discovered that there is a relationship between the acidic metal carbonyl hydride concentration in an organic liquid and the conductivity and pH of the solution. The relationship found between the metal carbonyl hydride concentration and the conductivity and pH of the solution allows for a simple and accurate measurement of metal carbonyl hydride concentration without the use of cumbersome wet-chemistry analytical techniques or expensive spectroscopic equipment. Thus, the method of the present invention may be used to control the removal of acidic metal carbonyl hydrides from organic liquids in a demetallating process.

In particular, the present invention provides a method for the determination of the concentration of cobalt carbonyl hydride in an organic liquid by measuring either the conductivity or pH of the organic liquid. The present invention allows for the degree of cobalt carbonyl hydride conversion to cobalt salts to be determined in a process stream in a continuous fashion. It has also been found that the conductivity and the pH of the crude aldehyde solution significantly decrease and increase, respectively, during the air decobalting step. Thus, the degree of decobalting can be determined in a process stream in a continuous fashion by using an on-line conductivity meter or an on-line pH meter. Efficient control of the continuous air decobalting process can be achieved by means of a feedback system from the on-line meter.

Upon further study of the specification and claims, further objects and advantages of this invention will become apparent to those skilled in the art.

DETAILED DESCRIPTION OF THE PREFERRED EMBODIMENTS

The method of the present invention is generally applicable to any acidic transition metal carbonyl hydride and derivatives thereof. Suitable metal carbonyl hydrides are those of Groups VI, VII, and VIII of the transition metals. Specifically, acidic metal carbonyl hydrides of Cr, Mo, W, Mn, Tc, Re, Fe, Ru, Os, Co, Rh, Ir, Ni, Pd, and Pt are suitable for use in the practice of the present invention. The metal carbonyl hydride may catalyze a process such as the homologation of alcohols, the carbonylation of cyclic ethers, dialkyl acetals, ortho esters, and esters, and the hydrogenation, hydrosilation, and hydroformylation of alkenes. It is preferred that the catalytic process be hydroformylation, i.e., the oxo process.

In its preferred embodiment, the present invention is applicable to the oxo conversion of any aliphatic or cycloaliphatic compound having at least one ethylenic carbon-carbon bond. Thus, it may be applied to the oxo process conversion of olefins having, e.g., from 2 to 20 carbons to reaction mixtures predominating in aliphatic aldehydes having one more carbon than the starting olefin. Suitable monoolefins include ethylene, propylene, and butylene. Suitable hydrocarbons include both branched- and straight-chain compounds having one or more terminal or internal olefinic sites. These sites may be conjugated, as in 1,3-butadiene, or non-conjugated, as in 1,5-hexadiene. In the case of polyolefins, it is possible to hydroformylate only one of the olefinic sites or several or all of the sites. The present invention may also be applied to the oxo conversion of ethylenic carbon-carbon bonds of functionalized hydrocarbons, such as unsaturated alcohols, unsaturated aldehydes, and unsaturated acids. It is preferred to apply the present invention to the oxo conversion of ethylene and propylene, because of the widespread use of such processes, frequently as continuous operations.

The process of the present invention may be applied to any oxo process using any catalyst source that is converted to an acidic metal carbonyl hydride under the reaction conditions. Catalyst sources that are converted to acidic carbonyl hydrides of Co, Fe, Ru, Rh, Ir, and Pt are preferred. Catalyst sources that are converted to acidic cobalt carbonyl hydrides are presently most preferred.

The metal, e.g., cobalt may be added to the reaction mixture in a variety of forms, e.g., as a cobalt salt, cobalt oxide, or dicobalt octacarbonyl. Other suitable catalyst sources include amine, arsine, stibine, phosphine, and phosphite derivatives of the metal carbonyl.

The amines, arsines, and stibines may be any trialkyl-, triaryl-, dialkylaryl-, or alkyldiarysubstituted moiety. Similarly, any trialkyl, triaryl, dialkylaryl, or alkyldiaryl phosphine or phosphite derivative of the metal carbonyl, particularly cobalt carbonyl, may be used as a catalyst source. U.S. Pat. 3,239,569 discloses a number of suitable catalyst sources which are phosphine derivatives and is incorporated herein by reference. The phosphine and phosphite derivatives of cobalt carbonyl are preferred, and cobalt carbonyl is particularly preferred.

The present invention comprises measuring either the conductivity or the pH of the organic fluid to be analyzed. It has been found that the conductivity of the organic liquid increases with increasing concentration of acidic metal carbonyl hydride. Thus, the concentration of acidic metal carbonyl hydride in the organic liquid can be ascertained by measuring the conductivity of the liquid.

Alternatively, the cobalt carbonyl hydride concentration may be determined by measuring the pH of the organic liquid by means of a pH meter. An increase in the pH of the organic liquid indicates a decrease in the concentration of acidic metal carbonyl hydride.

The present invention may be applied to any acidic metal carbonyl hydride containing organic liquid. It is preferred to apply the method of the present invention to product streams of catalytic processes, particularly aldehyde containing liquids.

A particular advantage of the present invention is the unexpected result that the contribution of metal salts to the conductivity of the oranic liquid is insignificant. Thus, thoroughly mixing a sample of air demetallated effluent with a water solution of ten times the normal effluent metal salt concentration produces an insignificant rise in the conductivity of the organic liquid. A further unexpected result of the present invention is that the pH of the liquid increases (becomes more basic) during air demetallating. It would be expected that the organic acids produced during air demetallating would increase the solution acidity and lower the pH.

The process of the present invention may be applied to the demetallating of an organic liquid in a batch process. Thus, during the air demetallating of a specific quantity of an organic liquid which also contains a quantity of metal carbonyl hydride, samples may be withdrawn and the concentration of metal carbonyl hydride determined by measuring either the conductivity or the pH of the liquid. The air demetallating of the organic liquid may be stopped when the measured conductivity of the sample is sufficiently low (or the measured pH of the sample is sufficiently high) to indicate an acceptably low concentration of metal carbonyl hydride. Alternatively, the conductivity or the pH of the organic liquid may be measured continuously during the air demetallating process and the process may be stopped when the measured conductivity is sufficiently low or the measured pH is sufficiently high.

In a preferred embodiment, the present method may be used in conjunction with a continuous air demetallating process. In a continuous air demetallating process, the crude product stream is mixed with air and fed into a demetallating unit. Oxidation of the acidic metal carbonyl hydride gives metal salts which are removed by washing with water. The conversion of metal carbonyl hydride to metal salts may be monitored by measuring either the conductivity or pH of the effluent from the demetallating unit. The measured conductivity or pH may be used to control the quantity of air fed into the continuous air demetallating unit by means of a feedback system.

Thus, if the measured conductivity rises to a level indicative of an unacceptably high concentration of metal carbonyl hydride in the effluent stream, the rate of air addition to the air demetallating unit can be increased until the measured conductivity drops to a level indicative of an acceptably low concentration of metal carbonyl hydride in the effluent. Alternatively, if the measured pH drops to a value indicative of an unacceptably high concentration of metal carbonyl hydride in the effluent, the rate of air addition to the air demetallating unit can be increased until the measured pH returns to a value indicative of an acceptably low concentration of metal carbonyl hydride in the effluent.

Similarly, when either the measured conductivity decreases or the measured pH increases to a value indicative of nearly complete demetallating and possible oxidation of product, the rate of air addition to the air demetallating unit can be decreased until either the measured conductivity increases or the measured pH decreases to a value indicative of minimal product oxidation.

One advantage of the present invention in conjunction with a continuous air demetallating unit is that neither the liquid flow rate nor the metal carbonyl hydride concentration entering the air demetallating unit need be accurately known to achieve an optimum oxygen to metal molar ratio. A further advantage of the present invention in conjunction with a continuous air demetallating unit is that an optimum oxygen to metal molar ratio may be achieved even when the liquid flow rate or the metal carbonyl hydride concentration entering the air demetallating unit varies with time.

Other features of the invention will become apparent in the course of the following descriptions of exemplary embodiments which are given for illustration of the invention and are not intended to be limiting thereof.

EXAMPLES

EXAMPLE 1

Cobalt Carbonyl Hydride Concentration Versus pH and Conductivity

This example illustrates the relationship between the cobalt carbonyl hydride concentration and the conductivity and pH in an organic solution. A sample of crude aldehyde feed to a continuous air decobalter was batch air decobalted in the laboratory. The rate of decobalting was followed by conductivity (bench top YSI conductivity meter) and pH measurements. The concentration of metal carbonyl hydride, in units of $Co_2(CO)_8$, was determined by decomposing the cobalt carbonyl hydride and measuring the quantity of carbon monoxide off gas. The total cobalt concentration was determined by atomic absorption spectroscopy. The results of this experiment are shown in Table I.

TABLE I

| Relationship Between Cobalt Carbonyl Hydride Concentration and Conductivity and pH | | |
|---|---|---|
| Cobalt Carbonyl Hydride (ppm $Co_2(CO)_8$) | Conductivity (microohms) | pH |
| 2 | 4 | 5.80 |
| 6 | 6 | 5.75 |
| 18 | 20 | 5.70 |
| 58 | 29 | 5.60 |
| 112 | 35 | 5.10 |
| 170 | 42 | 4.45 |
| 200 | 46 | 3.90 |

EXAMPLE 2

Conductivity and pH Measurements of the Crude Aldehyde Feed and Effluent of a Continuous Air Decobalting Unit The crude aldehyde feed and effluent of a continuous air decobalter were analyzed for conductivity and pH over a six-day period. The conductivity was measured with a TBI conductivity meter. The cobalt carbonyl hydride concentration was determined as described in Example 1. The average results of the six-day monitoring period are shown in Table II, and demonstrate that the conductivity and pH measurements obtained from the continuous air decobalter reproduce the values obtained in the batch air decobalting experiment.

TABLE II

Analysis of the Air Decobalter Feed and Effluent

| Decobalter Feed | | | Decobalter Effluent | | | |
|---|---|---|---|---|---|---|
| Total Cobalt,* ppm | Conductivity microohms | pH | Cobalt, ppm Total | Carbonyl Hydride | Conductivity microohms | pH |
| 284 | 54 | 4.1 | 34 | 8.2 | 8.8 | 5.9 |

*As Cobalt Carbonyl

EXAMPLE 3

Effect of Cobalt Salts on the Conductivity of the Air Decobalter Effluent

A sample of effluent (100ml) from the air decobalter taken durng the six-day monitoring period having a conductivity of 7.6 microohms was combined with 50 ml of water containing 6,000 ppm cobalt primarily in the form of cobalt formate and thoroughly mixed. The resulting solution had a conductivity of 7.8 microohms, as measured by a bench top YSI conductivity meter. The quantity of cobalt salt used in this example represents 10 times the normal quantity present in the decobalter effluent, thus it is readily recognized that the contribution of the cobalt salts to the organic solution conductivity is insignificant.

Obviously, numerous modification and variations of the present invention are possible in light of the above teachings. It is therefore to be understood that within the scope of the appended claims, the invention may be practiced otherwise than as specifically described herein.

We claim:

1. A method for controlling the quantity of air added during an air demetallating process of an organic liquid containing an acidic transition metal carbonyl hydride, comprising the steps of:
   (i) measuring the change in the electrical conductivity or pH of said organic liquid with a measuring device; and
   (ii) controlling said quantity of air added by a means of feedback from said measuring device.

2. The method of claim 1, wherein said measuring device is an on-line conductivity meter.

3. The method of claim 1, wherein said measuring device is an on-line pH meter.

4. The method of claim 1, wherein said demetallating process is an air decobalting process.

5. The method of claim 1, wherein said organic liquid is a product stream from a catalytic process selected from the group consisting of homologation of alcohols, carbonylation of cyclic ethers, carbonylation of dialkyl acetals, carbonylation of ortho esters, carbonylation of esters, hydrogenation of alkenes, hydrosilation of alkenes, and hydroformylation of alkenes.

6. The method of claim 5, wherein said catalytic process is hydroformylation of alkenes.

7. The method of claim 1, wherein said air demetallating process is a batch process.

8. The method of claim 1, wherein said air demetallating process is a continuous process.

* * * * *